US008951187B2

(12) United States Patent
Anderson et al.

(10) Patent No.: US 8,951,187 B2
(45) Date of Patent: Feb. 10, 2015

(54) INTRAORAL IMAGING SYSTEM

(75) Inventors: David Ryan Anderson, Royal Oak, MI (US); Daniel Joseph McCarthy, Troy, MI (US); Caitlin Elizabeth McCarthy, Troy, MI (US); Alexander Munro, Bloomfield Hills, MI (US); Raime Phillips, Rochester, MI (US)

(73) Assignee: Top Solutions, LLC, Troy, MI (US)

( * ) Notice: Subject to any disclaimer, the term of this patent is extended or adjusted under 35 U.S.C. 154(b) by 88 days.

(21) Appl. No.: 13/547,740

(22) Filed: Jul. 12, 2012

(65) Prior Publication Data
US 2013/0034825 A1 Feb. 7, 2013

Related U.S. Application Data

(60) Provisional application No. 61/514,117, filed on Aug. 2, 2011, provisional application No. 61/506,786, filed on Jul. 12, 2011.

(51) Int. Cl.
*A61B 1/05* (2006.01)
*A61B 1/00* (2006.01)
*A61B 1/247* (2006.01)
(52) U.S. Cl.
CPC ......... *A61B 1/00066* (2013.01); *A61B 1/00183* (2013.01); *A61B 1/00188* (2013.01); *A61B 1/247* (2013.01)
USPC .............................. 600/112; 600/476; 433/29
(58) Field of Classification Search
USPC ......... 600/476, 112, 120, 128, 129, 176, 187; 433/29, 215; 348/66
See application file for complete search history.

(56) References Cited

U.S. PATENT DOCUMENTS

| | | | |
|---|---|---|---|
| 4,697,577 A | 10/1987 | Forkner | |
| 5,762,603 A | 6/1998 | Thompson | |
| 5,908,294 A | 6/1999 | Schick | |
| 6,132,211 A | 10/2000 | Peithman | |
| 6,371,909 B1 | 4/2002 | Hoeg | |
| 6,560,013 B1 | 5/2003 | Ramsbottom | |
| 6,648,817 B2 | 11/2003 | Schara et al. | |
| 6,761,561 B2 | 7/2004 | Mandelkern | |
| 7,175,593 B2 | 2/2007 | Durell | |
| 7,182,728 B2 | 2/2007 | Cubb et al. | |
| 7,374,533 B2 | 5/2008 | Hoeg | |
| 2004/0114034 A1 | 6/2004 | Squilla et al. | |
| 2007/0032960 A1 | 2/2007 | Altmann et al. | |
| 2012/0040305 A1* | 2/2012 | Karazivan et al. | ............... 433/29 |

FOREIGN PATENT DOCUMENTS

WO WO2010034107 4/2010

* cited by examiner

*Primary Examiner* — Michael Rozanski
(74) *Attorney, Agent, or Firm* — Oakland Law Group, PLLC

(57) ABSTRACT

An intraoral imaging system includes a receiving module that communicates with an imaging display device. The imaging device includes handle having a transmitter module and a power source as well as neck and head portions that extend from the handle. The device includes a camera module that rotates in the distal and proximal direction to view and process still images and video. The camera module includes a movable image sensor to provide focus capability. The imaging device further includes a control assembly having a plurality of control members. The control assembly includes image capture controls that an operator engages in a lateral motion to capture images or video. A focus control member controls the spatial relationship between the image sensor and the stationary lens and an articulation control member to articulate the camera module to provide a greater range of imaging.

20 Claims, 10 Drawing Sheets

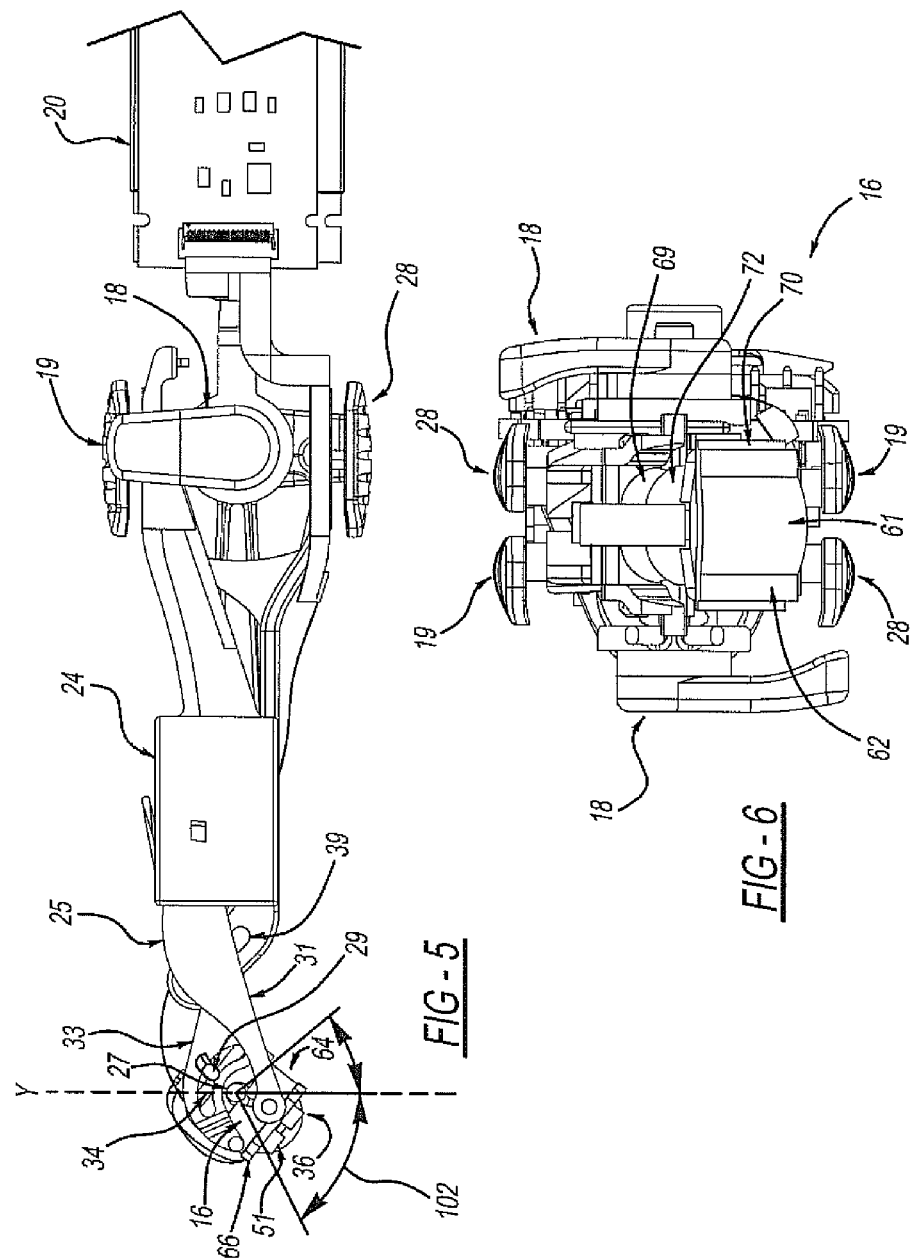

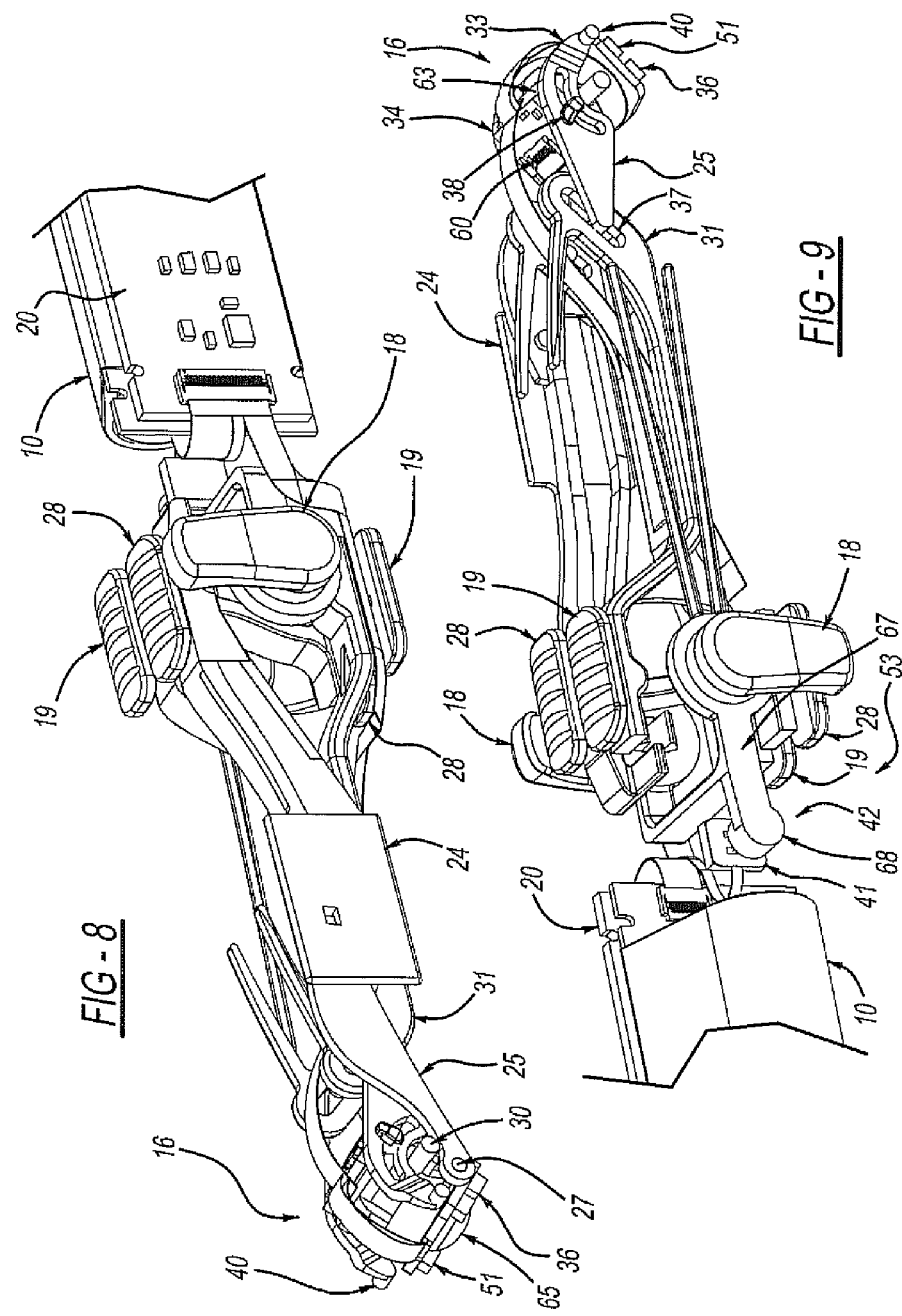

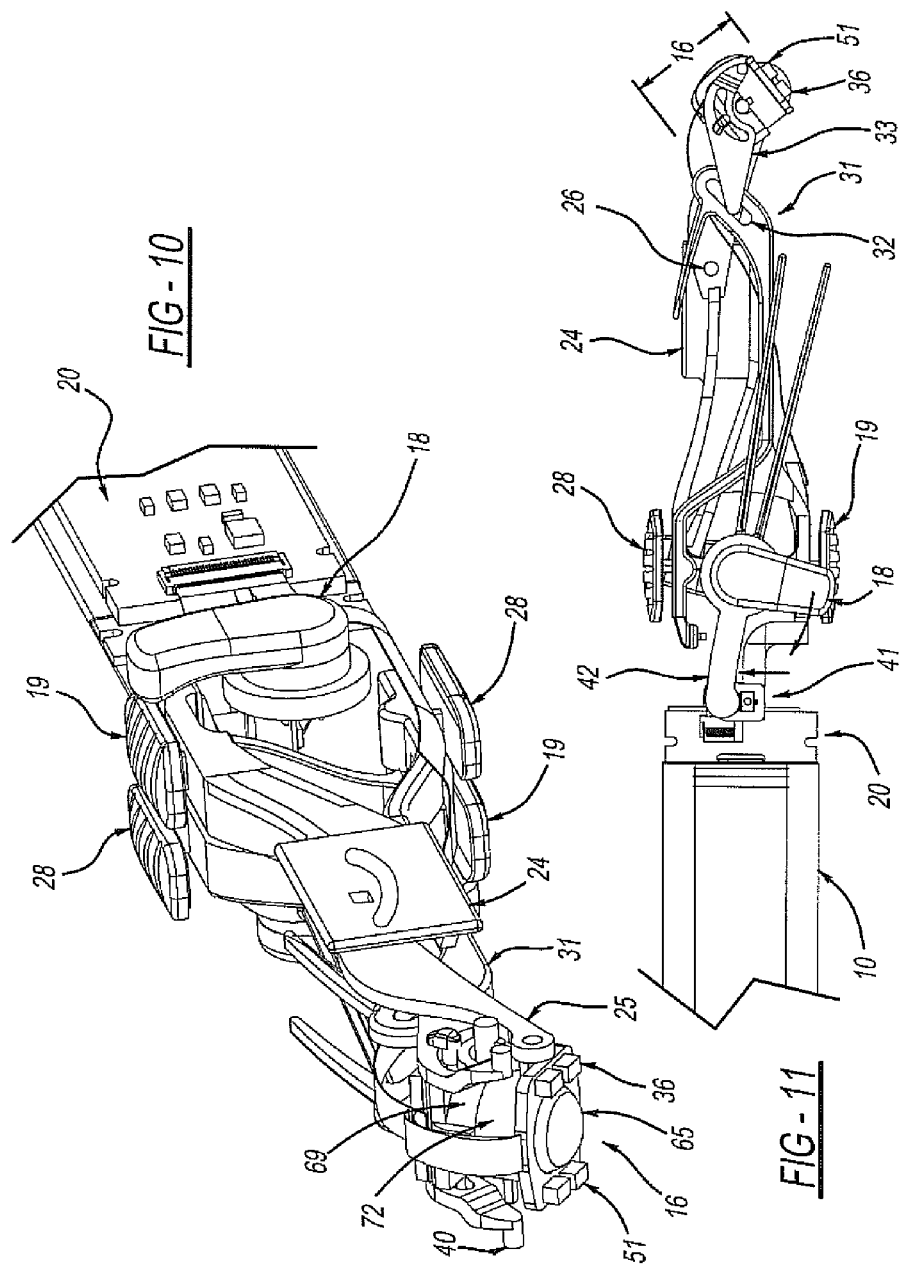

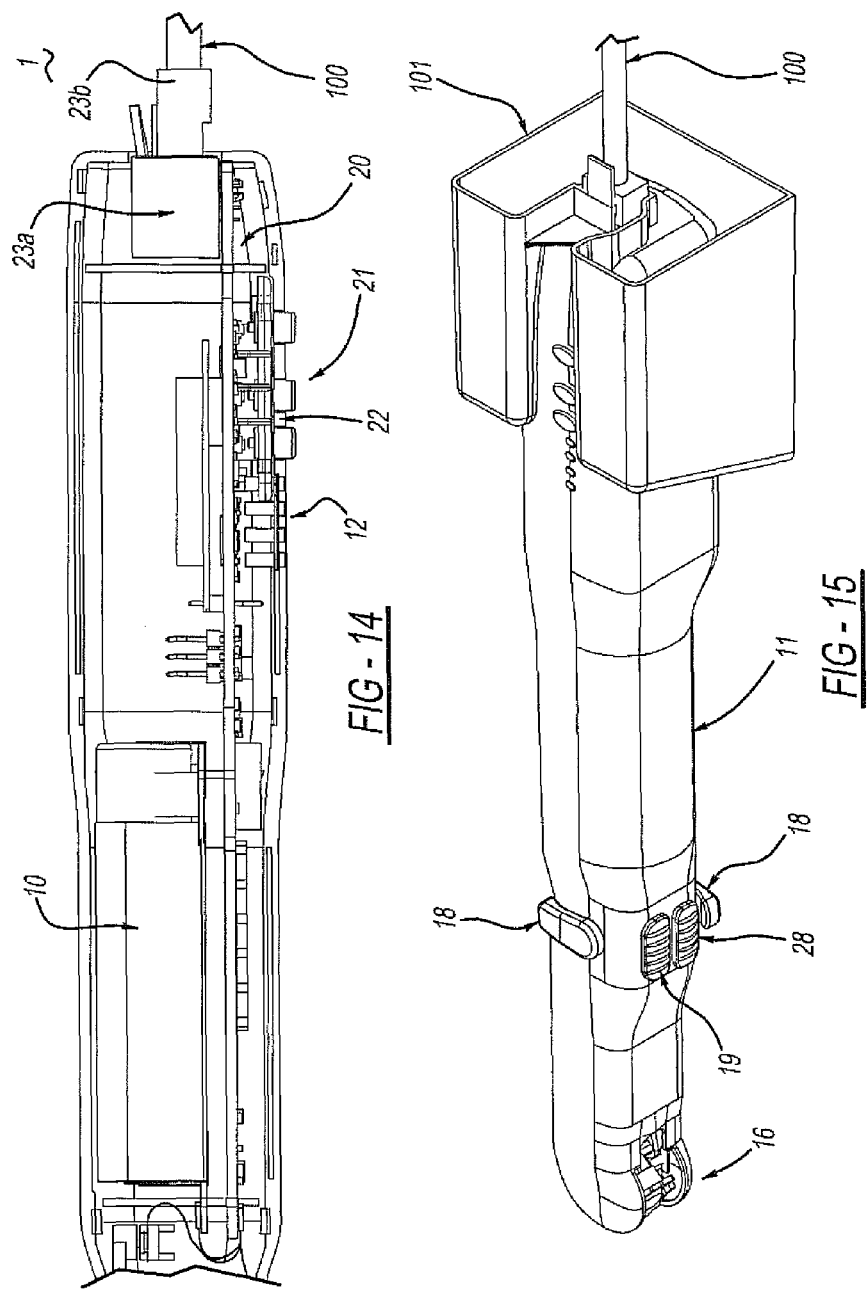

INTRAORAL IMAGING SYSTEM

CROSS-REFERENCE TO RELATED APPLICATION(S)

The present application claims priority to U.S. provisional applications 61/506,786 filed Jul. 12, 2011 and 61/514,117 filed Aug. 2, 2011, both of which are incorporated herein by reference in their entireties.

BACKGROUND OF THE INVENTION

1. Field of the Invention

The present invention relates, generally, to imaging systems. More specifically, the present invention relates to an intraoral imaging system for use in dental applications.

2. Description of the Related Art

Intraoral imaging systems are generally used in the fields of dentistry and orthodontics to capture video and still images during examinations and procedures in dental operatories. Intraoral imaging systems generally include a camera located along the distal end of an elongated apparatus. The camera is fixed relative to the apparatus which requires the operator to articulate the entire apparatus within a patient's mouth to capture a desired image or video. A prism is used to redirect the light reflecting off of nearby surfaces toward the remotely-located camera. This arrangement results in a limited field of operation for the camera. As a result, current imaging systems do not allow images to be captured in the distal direction which is useful for looking down a patient's throat, as well as allowing types of dental images not possible with current imaging systems. Some current imaging systems utilize software that is configured to accept data from a USB cable input directly from a video chip, such as the eMPIA® chip by eGalax_eMPIA Technology Inc. One disadvantage in using a USB cable to transmit images is the limited effective length of USB cables. Other current imaging systems wirelessly transmit image data. In this arrangement, a video chip is included in the hand-held device. Since the video chip is digital, the image data is sent wirelessly to the receiver in digital form, resulting in a large amount of data to be sent to the receiver where the receiver must process the data signal and convert it into a USB form before transmitting it to the computer imaging device. Actuating the still image capture feature of these cameras requires the operator to press downwardly on the apparatus. The downward application of force on the apparatus has been known to cause unintentional movement of the camera, which results in image distortion or capturing the wrong or unintended image. As a result, intraoral imaging systems known in the related art suffer from the deficiencies of fixed cameras; namely cumbersome articulation requirements and non-ergonomic still image capture capabilities. Accordingly, there is a need in the art for an intraoral imaging system that overcomes these deficiencies. More specifically, there is a need in the related art for an intraoral imaging system that includes a camera module that articulates within the device. There is also a need in the related art for an intraoral imaging system that provides greater ergonomic still image capture capabilities.

SUMMARY OF THE INVENTION

The present invention overcomes many limitations and disadvantages in the related art of intraoral imaging systems for use in dental applications. To this end, the intraoral imaging system of the present invention includes a receiving module with a video processing chip and an imaging device that is adapted to capture and transmit video and image signals to the receiving module. The intraoral imaging device further includes a camera module and a control assembly that is operatively linked to the camera module and adapted to actuate the camera module in a rotational manner relative to the horizontal axis of the imaging device. The intraoral imaging device further includes an image capture member that is adapted to direct the camera module to capture a still image through lateral contact of the capture member by the user.

Objects, features and advantages of the present invention will be readily appreciated as the same becomes better understood after reading the subsequent description taken in connection with the accompanying drawings.

BRIEF DESCRIPTION OF THE DRAWINGS

FIG. 5 is a partial cutaway side view of the articulation and focus sub-assemblies of the intraoral imaging system in accordance with at least one embodiment of the present invention.

FIG. 6 is a front side cutaway view of the intraoral imaging system in accordance with at least one embodiment of the present invention where the head portion is shown.

FIG. 8 is an isometric view of the articulation and focus sub-assemblies of the intraoral imaging system in accordance with at least one embodiment of the present invention.

FIG. 9 is a reverse isometric view of the articulation and focus sub-assemblies of the intraoral imaging system in accordance with at least one embodiment of the present invention.

FIG. 10 is an enlarged isometric view of the articulation and focus sub-assemblies of the intraoral imaging system in accordance with at least one embodiment of the present invention.

FIG. 11 is a partial side cutaway view of the articulation, focus and image capture sub-assemblies of the intraoral imaging system in accordance with at least one embodiment of the present invention.

FIG. 14 is a partial cutaway view of the intraoral imaging system in accordance with at least one embodiment of the present invention.

FIG. 15 is an overall view of the intraoral imaging system in accordance with at least one embodiment of the present invention.

DETAILED DESCRIPTION OF THE PREFERRED EMBODIMENT(S)

Figure 1:
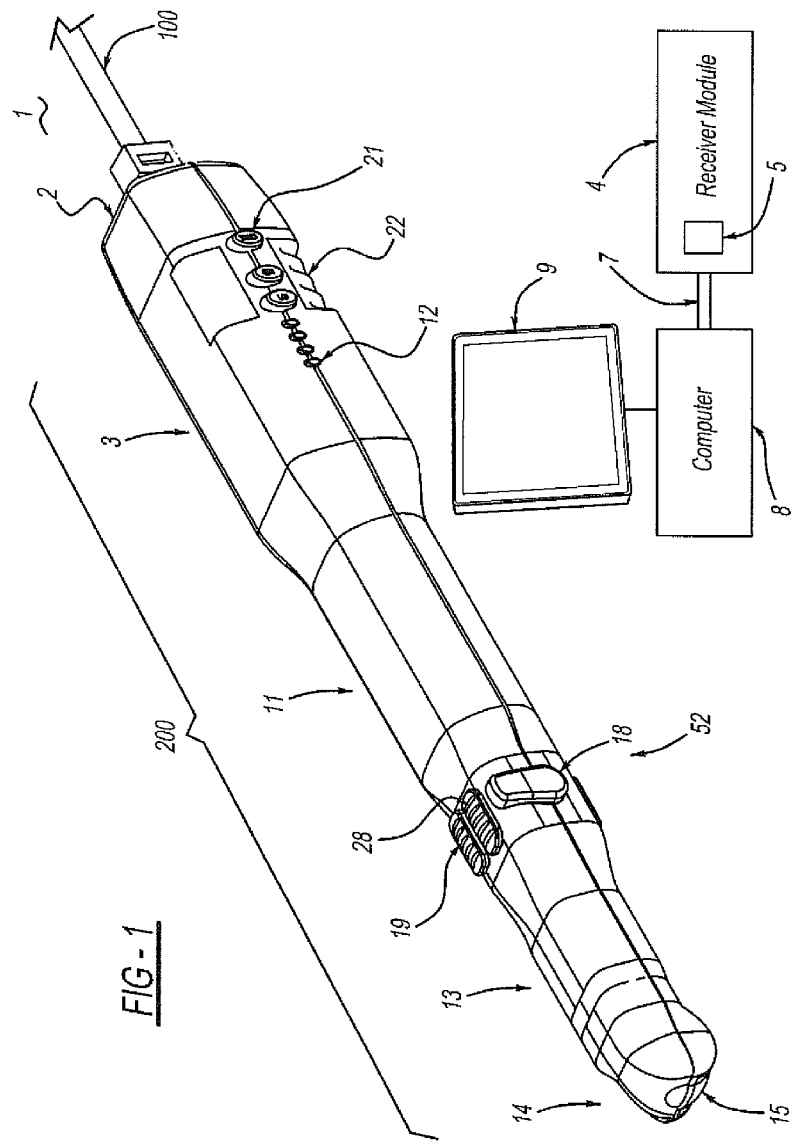
FIG. 1 is an overall side view of the intraoral imaging system in accordance with at least one embodiment of the present invention with the receiver module operatively engaged to a computer and an imaging display device.
Figure 3:
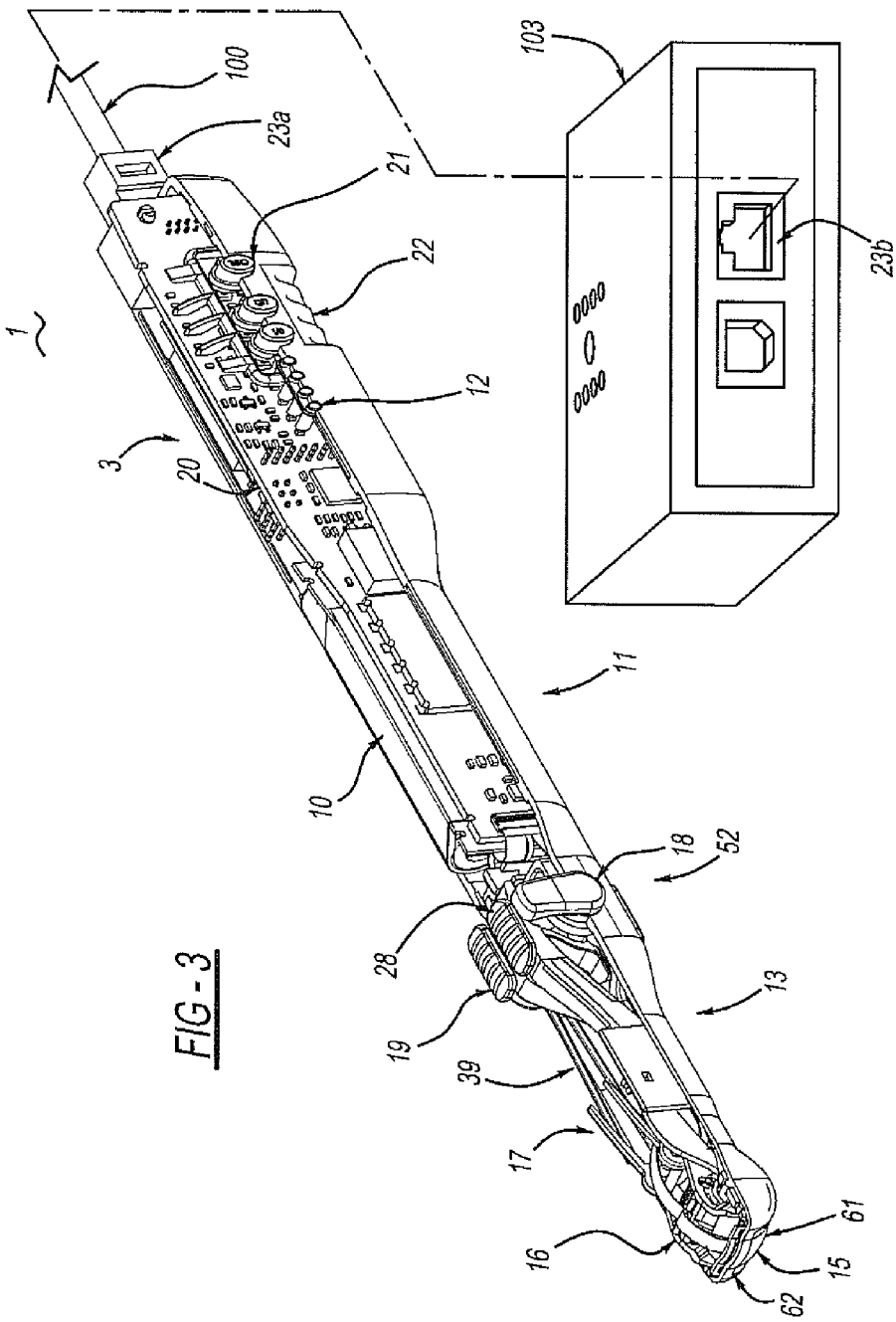
FIG. 3 is a partial side view of the intraoral imaging device according to at least one embodiment of the present invention, with half of the housing removed illustrating the internal components of the device.
Figure 4:
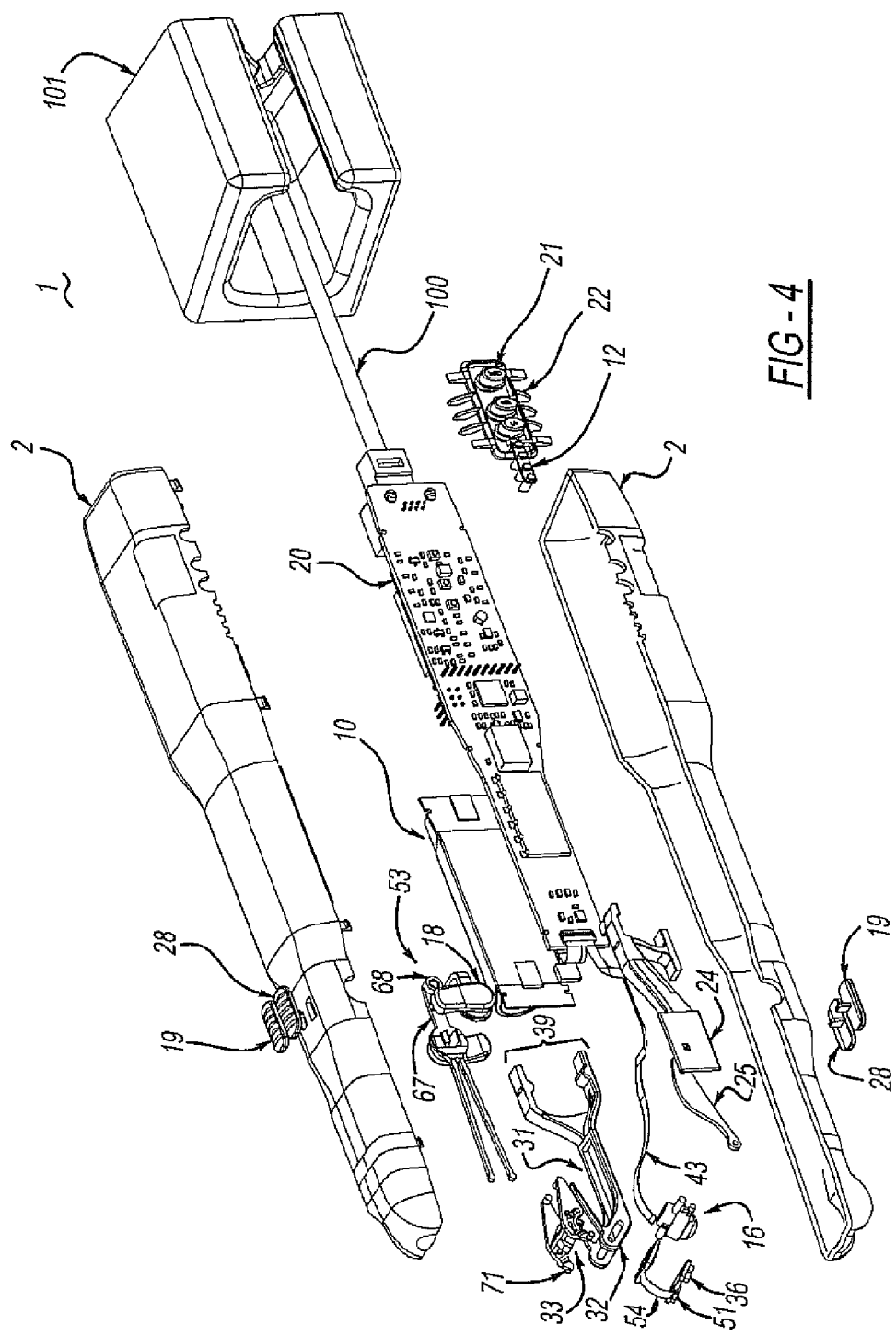
FIG. 4 is an exploded view of the intraoral imaging system in accordance with at least one embodiment the present invention.

The imaging system 200 is shown generally throughout the Figures. Referring now to FIG. 1, one embodiment of the intraoral imaging system 200 is shown. The imaging system 200 includes intraoral imaging device 1 that is adapted to capture still images and video/motion images and other data (collectively, "data") and a receiver module 3 that is adapted to electronically communicate with and receive data from the imaging device 1. More specifically, the imaging device 1 includes transmitter module 3 to transmit data to the receiver module 3 (FIGS. 3 & 4). It should be appreciated that the intraoral imaging device 1 is adapted for use in connection with dental and orthodontic examinations/procedures/applications; however, imaging device 1 may be used in other applications where the qualities and attributes of the device 1 may be beneficial, such as an industrial inspection camera.

Figure 2:
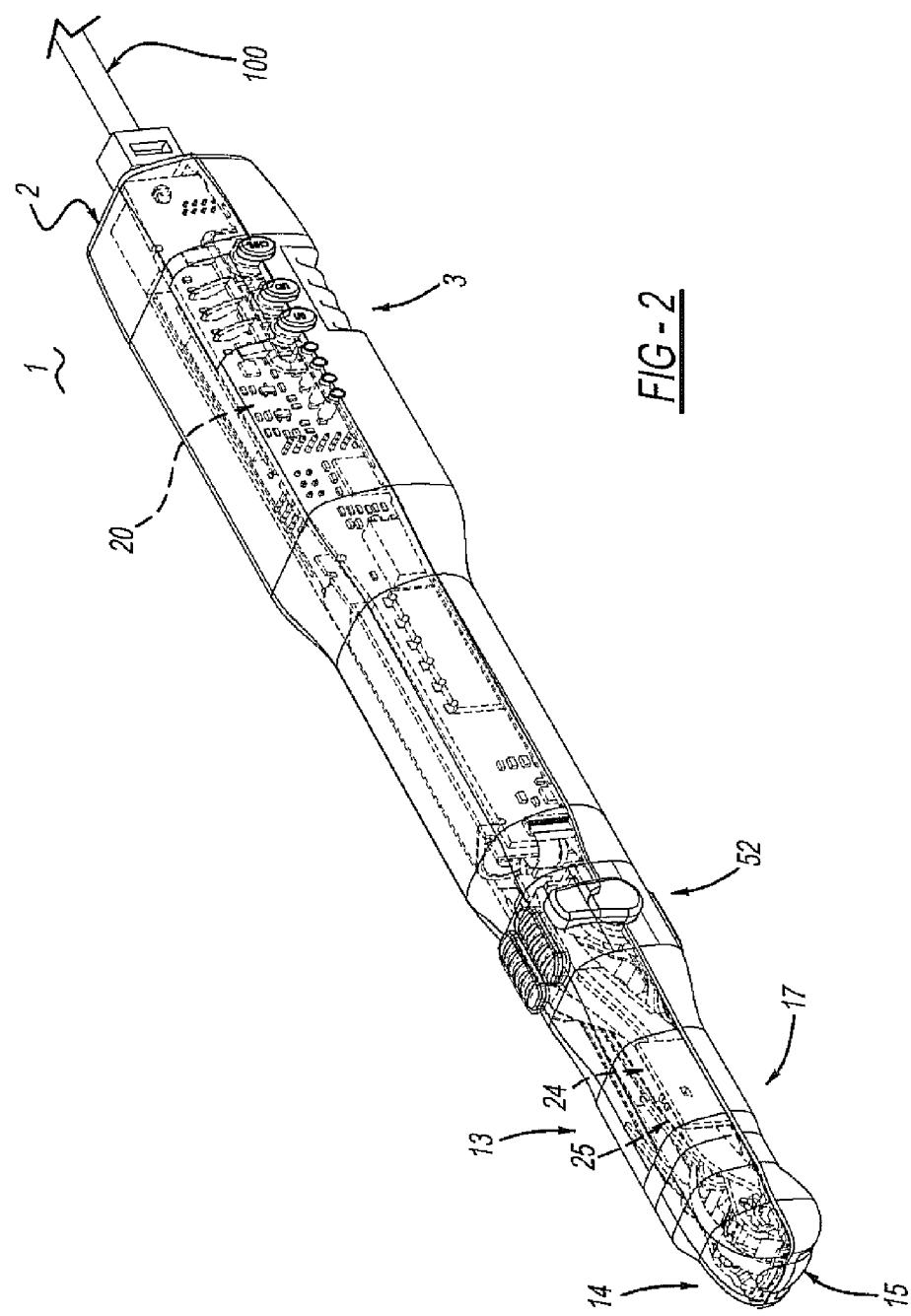
FIG. 2 is a partial cutaway side view of the intraoral imaging system in accordance with at least one embodiment of the present invention that illustrates a connection to a data link.

As illustrated in FIGS. 1 and 2, the transmitter module 3 and receiver module 4 each further include an input port 23a & 23b (as shown in FIG. 3), respectively, that are adapted to receive a data cable 100 to provide a "hardwire" connection therebetween. Those having ordinary skill in the art will appreciate that the input ports 23a & 23b (as shown in FIG. 14) may be configured to receive a Universal Serial Bus (USB) cable or Category Five or Six (Cat5 or Cat6) Ethernet cable, or another cable suitable to facilitate hardwire communication. As various cables have different performance characteristics, a particular cable may be more suitable for use in one application of the system according to the present invention over another cable. For example, a USB cables are not able to transmit data over long lengths, such as beyond 15 feet. In contrast, Cat5 or Cat6 cable can safely and consistently transmit data over hundreds of feet. One skilled in the art would recognize that depending upon the distance required to transmit signals, an appropriate length cable is to be selected.

The receiver module 4 includes a video processing chip 60 (as shown in FIG. 9) such as an eMPIA© video chip for processing video and image data transmitted from the imaging device 1. The receiver module 4 is further adapted to provide a communicative link between the imaging device 1 and an imaging display device 9 shown generally in FIG. 1 as a computer and monitor. However, those having ordinary skill in the art will appreciate that the imaging display device 9 may include a Personal Digital Assistant (PDA), smart phone, tablet, or other similar device suitable for displaying an image captured by the intraoral imaging device 1. The receiver module 4 includes a USB cable 7 to removably engage the imaging display device 9. Those having ordinary skill in the art will appreciate that while a USB cable 7 between the imaging display device 9 and the receiving module 4 is shown in FIG. 1, other manners of interface that accomplish the intended objective are anticipated. By way of example, the receiver module 4 may include a wireless transmitter to relay signals between the transmitter module 3 and the imaging display device 1. Further by way of example, the receiver module 4 may be operatively engaged to an imaging display device 9 in a fixed or internal manner.

Figure 7:
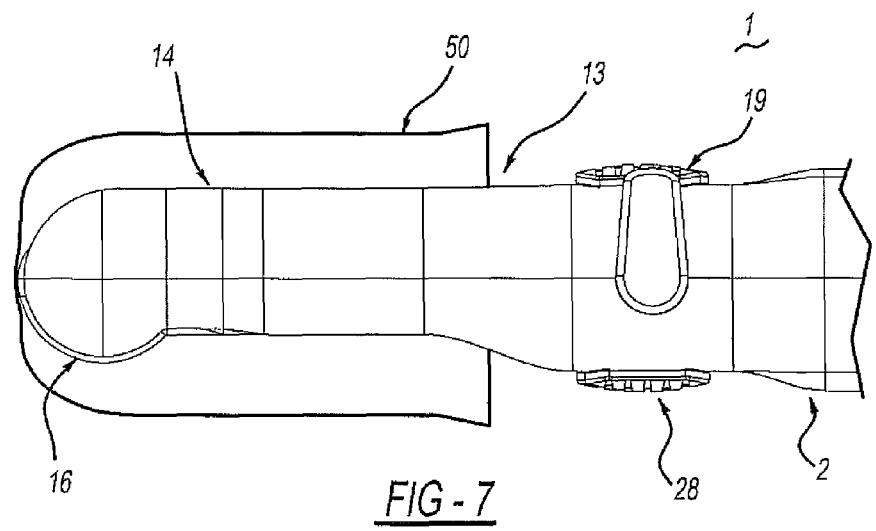
FIG. 7 is a partial side view of at least one embodiment of the present invention including the protective sheath over the head and neck portions.
Figure 12:
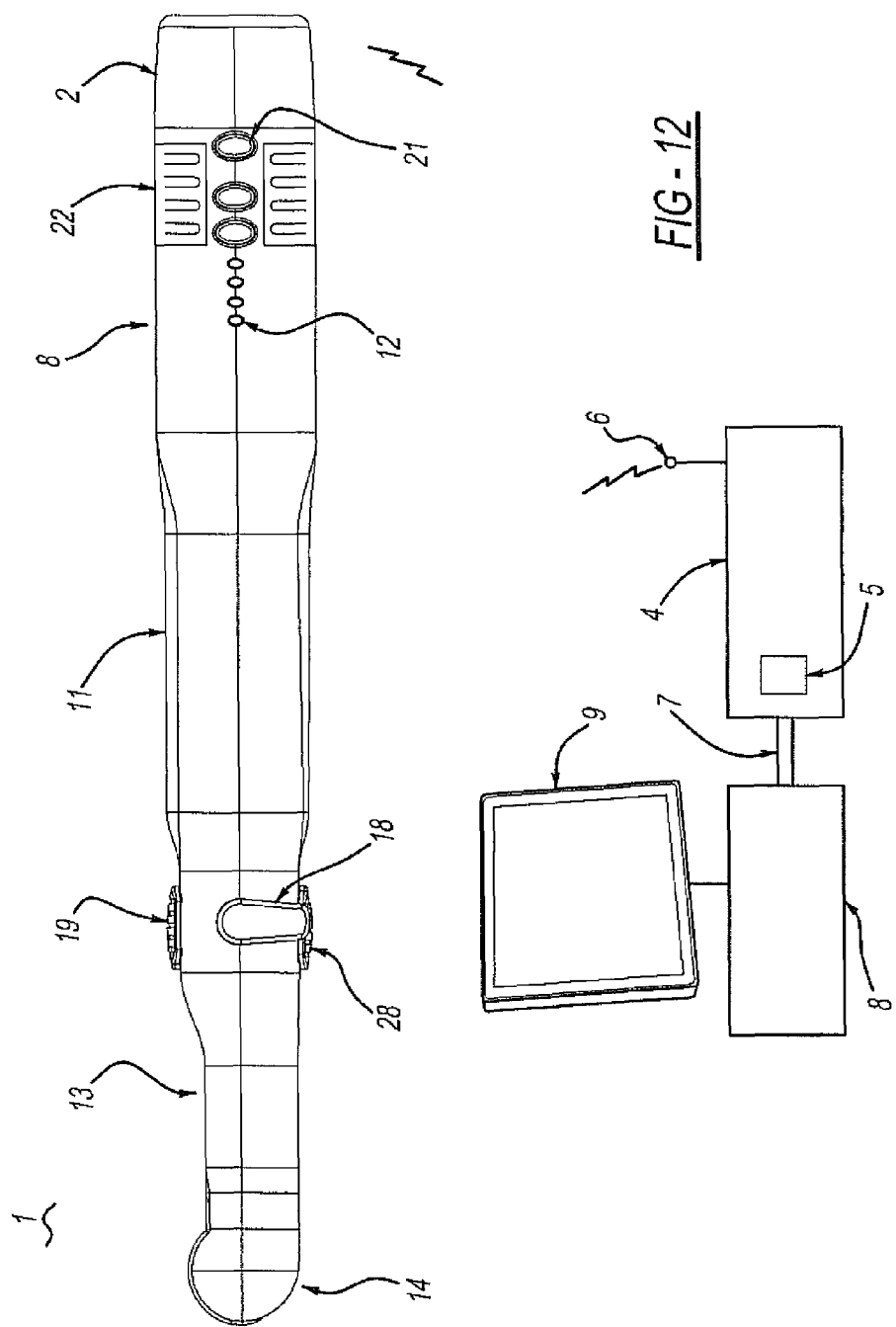
FIG. 12 is an overall side view of the intraoral imaging system in accordance with at least one embodiment of the present invention.

Referring to FIGS. 1 and 2, the housing 2 of the intraoral imaging device 1 includes a housing 2 having a head portion 14 and a neck portion 13 that depends from the head portion. The neck 13 and head portions 14 retain slender cross-sectional profiles relative to the remaining portion of the housing 2. Although there are apparent variations in overall profile within the head portion 14 and neck portion 13 (as shown in FIGS. 7 and 12), the cross-sectional areas of these two portions 13 & 14 are the same circumference by virtue of utilizing the Whitcomb area rule technique traditionally employed in the aerospace industry. Providing a head portion 14 and neck portion 13 with the same circumference, enables the present invention 200 to employ conventional dental hygienic sheaths. The head portion 14 further includes a window 15 defined therein through which a camera module (to be described) is utilized. The window 15 includes a spherical center section 61 and a non-spherical section 62. The window 15 is operatively engaged to the housing 1 so as to provide a water-tight seal therebetween and adapted to protect the camera module 16 (to be described) and is constructed such that it does not impact the ability of the camera module 16 to capture images or video, including a spherical portion to prevent image distortion. Those having ordinary skill in the art will appreciate that the spherical center section 61 is capable of providing a magnification/enlarging feature to the camera module.

As shown throughout FIGS. 3 and 4, the intraoral imaging device 1 includes a camera module 16 operatively disposed within the head portion 14 of the housing 2. The camera module 16 rotates within the head portion 14 adjacent to the window 15, which has a spherical center section 61 to preclude image distortion as the camera module 16 is rotated and a movable image sensor 34 that is disposed in distal relation relative to the window 15. Image sensor 34 is mounted to a movable frame 63 to provide a focusing aspect to the camera module 16. More specifically, the movable image sensor 34 is adapted to move fore and aft relative to the rotating lens elements 64 of the camera module 16 in order to provide proper focus for the subject matter of the image. The movement of the movable image sensor 34 will be discussed in greater detail below. As shown in FIG. 5, the movable image sensor 34 is a chip that is defined as a CMOS (complementary metal-oxide semiconductor) or CCD (charge-coupled device) chip to provide images (in the native resolution of the readily-available dental management software). It should be understood that other suitable chips may be used that are adapted to achieve the intended observation of the captured image and video data. Accordingly, the movable image sensor 34 may capture images in 640×480 resolution or capture images in a higher resolution (i.e. 1280×960) and process images to a smaller resolution having improved quality. Those having ordinary skill in the art will appreciate that the movable image sensor 34 will process images received from the lens 65 of the camera module 16 in a resolution and formats that is most commonly accepted or readily converted by software that is employed by the dental industry.

The camera module 16 further includes a primary lighting element 36. The primary lighting element 36 (as shown in FIGS. 4 and 5) is adapted to illuminate the subject matter of the image to be captured by the movable image sensor 34. The primary lighting element 36 may include a plurality of light emitting diodes (LEDs) that are affixed to a panel that is disposed adjacent to the rotating lens elements 64 of the camera module 16 and a plurality of LEDs affixed to the camera processing electronics 43. The juxtaposition of the primary lighting element 36 relative to the rotating lens elements 64 of the camera module 16 such that the primary lighting element 36 is recessed from the focal lens plane 66 to reduce the likelihood of back reflectance into the camera lens 65 of the camera module 16. Those having ordinary skill in the art will appreciate that the primary lighting element 36 may be defined by an illumination component that differs from an LED such as an incandescent or fluorescent light. However, based on the limited sizing requirements within the head and low power requirements, LEDs are the current preferred source of illuminating the subject matter.

The camera module 16 may further include a secondary lighting element 51 that is adapted to further illuminate the field of view. The secondary lighting element 51 may be adapted to operate simultaneously with the primary lighting element 36 or independent therefrom. The secondary lighting element 51 includes a light source that differs from the primary lighting element 36 to provide a diagnostic tool or other functional component to the intraoral imaging system 200. By way of example, the secondary lighting element 51 may provide a blue light source that projects light within the 400 nm-499 nm wavelength range. Light having a wavelength within the aforementioned wavelength range has demonstrated the capability of identifying potential differences in teeth and/or oral tissue. Accordingly, a secondary lighting element 51 that provides a wavelength within the 400-499 nm range would provide the intraoral imaging system 200 with an additional diagnostic tool to identify potential differences in the teeth and/or tissue in the oral cavity.

Referring generally to the FIGS. 1 and 2, the intraoral imaging device 1 further includes a control assembly 52 that is operatively disposed between the neck portion 13 and the handle portion 11 and provides an operator interface to control the camera module 16. As will be described in greater detail below, the control assembly 52 includes image capture, camera focus, and camera articulation controls 18, 19, and 28 respectively, that are adapted to enable the operator of the device 1 to manipulate the camera module 16 in a desired manner. The control assembly 52 includes an image capture sub-assembly 53 (as shown in FIG. 9). The image capture sub-assembly includes image capture controls 18 that are manually engaged by the operator and adapted to direct the camera module 16 to capture a still image as well as record/stream video to the transmitter module 3.

Imaging systems known in the art require downward application of force to capture an image or record video which can result in distorted imaging and unintended articulation of the imaging system. Unlike known imaging systems, the image capture controls 18 are adapted to be actuated in the fore/aft direction relative to the imaging device 1 to capture the image or stream video. By changing the force vector for image capture in the longitudinal direction, the image capture controls 18 reduce the likelihood of capturing distorted images and stabilize the operator's articulation of the imaging device 1 during operation.

To this end, the imaging capture controls 18 provide an ambidextrous build that is adapted to be actuated by the operator's index finger along the top side of the imaging device 1. Redundant controls are located on the top and bottom side of the housing 2. To optimize the device 1 for right or left handed operation the image capture controls 18 are configurable. For left-handed users the upward position of the image capture control 18 will be on the left side, whether the device 1 is pointed camera-up or camera-down. For right-handed users the upward position of the image capture control 18 will be located on the right hand side. This allows finger reach to be minimized providing enhanced ergonomics. Those having ordinary skill in the art will appreciate that the configurable nature of the dual image capture controls 18 provide the added benefit to the user of being able to invoke an image capture action in a similar manner regardless of the orientation of the device 1 and regardless of whether the device 1 is being used by a left-handed or right-handed person. This is an important functionality as intraoral imaging cameras are used to capture images of upper and lower teeth of a patient.

Providing similar capture capability on both the top and bottom of the device 1 allows for ergonomically correct image capture whether the device 1 is being used in camera-up or camera-down orientation, thereby eliminating the operator to reposition relative to the patient. This control arrangement allows the operator to use the device 1 with the camera module 16 pointing downward to examine a patient's upper teeth or rotate the device 1 over 180 degrees (top to bottom) to capture images of the patient's lower teeth (in the situation where the patient is inclined in front of the operator with top of the patient's head proximal to the doctor). The device 1 operates identically whether camera module 16 is pointing upwards or downwards.

The image capture subassembly 53 includes a Hall Effect sensor 41 located at a predetermined position and capture arm 67 having a magnet 42 defined thereon that cooperate to engage the image capture feature of the present invention. The image capture subassembly 53 further includes a central point 68 about which the image capture control pivots in order to capture the image. More specifically, during "standby operation," the magnet 42 and Hall Effect sensor 41 are positioned in proximate relation relative to each other such that the image capture/video record function is not engaged. When the operator of the device 1 desires to activate the image capture/video record feature, the image capture control 18 is manipulated so as to move the capture arm 67 within the housing 2 and place the magnet 42 in distal relation relative to the Hall Effect sensor 41, thereby changing the state of the Hall Effect sensor 41 and invoking the capture command. While a Hall Effect sensor and magnet operation has been described with respect to the image capture functionality of the device 1, those having ordinary skill in the art will appreciate that other structure may be suitable for invoking an image capture command within an intraoral imaging device in a longitudinal manner relative to the housing to accomplish the intended objective of minimizing image distortion as described above.

Referring to FIGS. 2-4, the control assembly 52 further includes an articulation control member 28 that is adapted to actuate the camera module 16 in a rotational manner within the head portion 14. The articulation control member 28 is adapted to actuate the camera module 16 within a predetermined range of movement 102 that is up to 60 degrees forward and 30 degrees backward relative to the vertical plane of the imaging device 1, shown as the Y-axis (as shown in FIG. 5). It should be further appreciated by those having ordinary skill in the art that the predetermined range of movement 102 may cover a range beyond of 60 degrees forward and 30 degrees backward, and that the values provided herein are exemplary in nature but without limitation.

The control assembly 52 further includes an articulation drive sub-assembly 17 that is operatively linked to the articulation control members 28. The articulation drive sub-assembly 17 includes an articulation rack 24 that is operatively engaged to the articulation control members 28 and an articulation link 25 that is coupled to the articulation rack 24. The articulation link 25 provides actuation of the articulation rack 24 in response to operator input on the articulation control members 28. The articulation link 25 extends from the articulation rack 24 toward the head portion 14 of the intraoral imaging device 1. The articulation rack 24 may be coupled directly to the camera module 16 by way of corresponding geared surfaces. However, those having ordinary skill in the art will appreciate that the articulation link 25 and articulation rack 24 may be operatively coupled in several manners that accomplish a similar objective. Furthermore, those having ordinary skill in the art will appreciate that the articulation rack 24 is configured in an X-like configuration to enable the articulation controls 28 to move in the same direction relative to the housing 2 regardless of which articulation control 28 is engaged by the operator. This functionality within an intraoral imaging device 1 provides for ambidextrous manipulation by the operator so as to reduce the likelihood of inadvertent/unwanted actuation of the camera module 16 during common usage practices for viewing upper and lower teeth of a patient.

The articulation drive sub-assembly 17 further includes an articulation pin 26 (as shown in FIG. 11) that are integral to the articulation rack 24 to facilitate connection to the articulation link 25. Additionally, the articulation drive subassembly 17 further includes a camera module articulation pin 27 that couples the articulation link 25 to the camera module 16. The articulation link 25, articulation pins 26, and camera module articulation pin 27 couple to rotate the camera module 16 about camera module pivot pin 30 in response to operator input to the articulation controls 28. More specifically, the camera module 16 is fixed to a portion of the articulation drive sub-assembly 17 and adapted to rotate in response to operator input on the articulation control member 28. As shown in the Figures, the camera module 16 is fixed to the articulation link 25 via camera module articulation pin 27, adjacent to the stationary lens 69 of the camera module 16. The camera module pivot pin rests within recesses defined in the cavity of the housing 2 (FIG. 3). Those having ordinary skill in the art will appreciate that the camera module 16 may be secured to any portion of the articulation drive sub-assembly 17 that will provide rotational movement of the camera module 16 within the predetermined range of movement 102 described above (i.e. 90 degrees).

The control assembly 52 further includes a focus control member 19 that is adapted to focus the camera module 16. More specifically, the focus control member 19 adjusts the spatial relationship between the movable image sensor frame 34 and the lens assembly 70 of the camera module 16. To this end, the control assembly 52 further includes a focus control subassembly 39 that is operatively linked to the focus control member 19 (FIGS. 3 & 4). The focus control sub-assembly 39 includes a focus control rack 31 that is engaged to the focus control member 19 and a focus control track and cam 33 that is coupled to the focus control rack 31. The focus control cam and track 33 includes focus rack slots 32 and focus rack pins 71 to couple the focus control rack 31 to the focus control cam and track 33. The operative engagement between the focus control rack 31 and the focus control track and cam provide actuation of the focus control cam and track 33 in response to operator input on the focus control member 19. The articulation within the focus rack slots 32 provide a limited range of movement for the focus control cam and track 33 which controls movement of the movable image sensor 34 relative to the stationary lens 69 of the camera module 16. The limited range of movement provides the predetermined span of adjustable focus for the camera module 16. To this end, it should be appreciated by those having ordinary skill in the art that the span of the focus rack slots 32 may vary in order to accommodate the intended amount of focal adjustment between the movable image sensor 34 relative to the stationary lens 69 of the camera module 16.

The focus control cam and track 33 further include a guide channel 37 (as shown in FIG. 9) that are adapted to operatively receive the frame pins 38 of the movable image sensor 34. The arcuate configuration of the guide channels 37 enable the movable image sensor frame pin 38 to remain engaged to the guide channels 37 as the camera module 16 is rotated so as to maintain the spatial relationship relative to the movable lens 72 throughout the predetermined range of movement 102 of the camera module 16. Generally speaking, the cooperation between the guide channels 37 and the movable image sensor frame pins 38 enable the camera module 16 to maintain focus during articulation of the camera module 16 through the range of movement 102. Importantly, the relationship between the guide channels 37 and the frame pins 38 further cooperate with the focus rack slots 32 in the focus control cam and track 33 to adjust focus regardless of the rotational orientation of the camera module 16. Those having ordinary skill in the art will appreciate that the focus control cam and track 33 and focus control rack 31 may be operatively coupled in several manners that accomplish a similar objective. By way of example, the focus control rack 31 and focus control cam and track 33 may be fixed together gears or rotating links.

As shown throughout the Figures, the control assembly 52 includes opposed focus control members 19 and opposed articulation control members 28. As discussed above, the purpose of the opposed control members is to provide for multiple manners of use by the operator. The focus and articulation control members 19 & 28 of the present invention are disposed along the top and bottom surfaces of the housing 2 to enable different control manipulation with minimal operator articulation. Those having ordinary skill in the art will appreciate that other variations of control members may be provided to accomplish the same end. By way of example, the control assembly 52 may include recessed wheels to provide a substantially similar operator articulation method.

The imaging device 1 includes a transmitter module 3 having at least one transmitter (not shown) that is operatively disposed within the cavity of the housing 2 as part of main electronics 20. The transmitter module 3 is adapted to receive image and video data from the camera module 16. The transmitter module 3 further includes a second transmitter (not shown) and the receiver module 4 further includes a second receiver 5 to send the image capture signal from the device 1 to the receiver module 4 to invoke a save image command using a hard-wired connection. In this way, the first transmitter/receiver combination is dedicated to sending video data and the second transmitter/receiver combination is dedicated to sending a capture command identifying which image frame to save electronically, if desired. An important aspect of this arrangement is that the video stream may be sent in analog or digital form to the receiver module 4 and the image processing chip located in the receiver module 4 to be output directly to the computer 8 via USB cable 7.

Previous dental management software packages are only capable of receiving data streamed through a USB cable directly from the industry-standard eMPIA© chip. Previous imaging systems locate the eMPIA© chip within the imaging device and connect to a computer directly using a USB cable. The present intraoral imaging system 200 uses, in one embodiment, a single transmitter in transmitter module 3 of the imaging device 1, with multiple video and audio channels. The video channel is dedicated to transmitting video data from the device 1 to the receiver module 4. The audio channel is dedicated to sending the capture command bit to identify the corresponding video frame to be saved. The receiver module 4 contains the receiver portion of the transmitter/receiver combination and receives both the video and audio (capture signal) data. A second embodiment utilizes the transmitter/receiver combination discussed previously to transmit only video data, while a second transmitter/receiver combination, using a low bandwidth, transmits the data required to command the image processing chip to save the current video frame to the imaging system 200.

In another embodiment, the imaging system 200 further includes a receiver module 4. The receiver module 4 includes a first receiver 5 that is adapted to wirelessly receive the video signal from the first transmitter 3. As illustrated in FIG. 1, the first receiver 5 within the receiving module 4 and the first transmitter (not shown) within the transmitter module 3 are adapted to communicate wirelessly, without a hard-wire connection. To this end, the receiver module 4 includes an antenna 6 that is adapted to receive the wireless signal transmitted by the transmitter module 3. In one embodiment, the transmitter module 3 also sends the image capture signal from the device 1 to the receiving module 4 to invoke a save image command using audio channels included in the transmitter/receiver pair.

In an alternative embodiment, the receiver module 4 further includes a second receiver 5 to wirelessly send the image capture signal from the device 1 to the receiving module 4 to invoke a save image command. It should be appreciated that the second transmitter-receiver pair is further adapted to provide a synchronization feature with respect to the image capture signal transmitted and received by the first transmitter and second transmitter, respectively. It should further be appreciated that the communication between the second transmitter and second receiver may also provide a failsafe or correction relative to the signal between the first transmitter and second transmitter.

The intraoral imaging device 1 also includes transmitter module 3, located at the opposite end of the head portion 14. The transmitter module 3 includes at least one transmitter for communicating images captured by the device 1 to external imaging devices 9 or other computers or devices. Also included in the transmitter module 3 is a plurality of battery indicator lights 12, which may be LEDs or other light-emitting devices. These battery indicator lights 12 display the current state of the onboard power source 10 within the intraoral imaging device 1. The battery indicator battery indicator lights 12 may be arranged in a number of possible ways, such as green-yellow-red to indicate high-to-low levels of charge, or another color arrangement may be used. In addition or alternatively, an audible sound may be emitted when charge levels reach certain thresholds, as well as near a fully-discharged state. These audible tones are beneficial for a user/operator that may be focused intently on the patient and not on the charge state of power source 10. Also, the charge state may be communicated by the device 1 through the imaging software of system 200, such as additional information to the user on the imaging display device 9, such as "Low Batt" or other icons, for example, which may appear on the display screen.

Further with regard to the transmitter module 3, a number of channel select LEDs 22 are provided in the device 1. Channel select LEDs 22 indicate which channel the imaging device 1 is currently using to transmit images, either hard-wired or wirelessly. Using the integrated channel selector contained in the main controls 21, a user/operator may cycle through the available channels—for example, eight—to match the device 1 frequency to the pre-set frequency of the receiver module 4 in the current operatory, allowing the same device 1 to be used in multiple operatories. The system 200 may also assist the user by only providing for use those frequencies which are available, to prevent any interference with other devices 1 that are currently being used and transmitting on a particular channel. For example, the user may push the channel selector main control 21 and the LEDs 22 will illuminate channels 1, 3, 4, 7, and 8 but not 2, 5, and 6 because those are currently being used by other devices 1 in range. The bottom portion of the transmitter module 3 of the imaging device 1 includes at least one input port 23 which engages with the docking station 101, for image transmission and power charging of the onboard power source 10. The input port 23 may accept a CAT5 or CAT6 cable connection, for example. An alternate embodiment may allow a USB connection, or other suitable cable connection.

Figure 13:
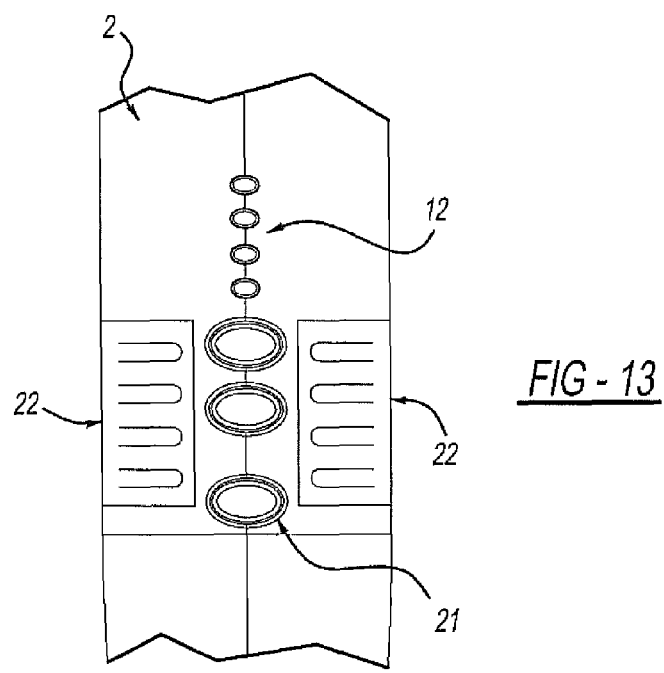
FIG. 13 is a close-up view of the main controls of the intraoral imaging system in accordance with at least one embodiment of the present invention.

Referring to FIG. 3, the imaging device 1 is illustrated in a partial cutaway view with a portion of housing 2 removed to show the power source 10 operatively disposed within the handle portion 11. The power source 10 for the device 1 may be a battery. Those having ordinary skill in the art will appreciate that power source 10 may be a rechargeable battery which may be charged by connecting to an Ethernet or other data cable which is connected to the docking station or disposable battery (not shown). Furthermore, those having ordinary skill in the art will appreciate that the housing 2 may include battery door (not shown) to provide access to the power source 10 for maintenance, recharging and/or replacement. It should further be appreciated that the power source 10 may be defined as a plurality of batteries in order to provide an acceptable level of usable life for the intraoral imaging device 1. By way of example, the power source 10 may be adapted to provide approximately 5 hours of operational use and 15 hours of standby time. On the imaging device 1, a plurality of battery level indicators 12 may be provided to indicate the current state of charge of the device 1. The power source 10 is shown located within the handle portion 11 of the device 1, which also contains a portion of the main electronics 20. The remainder of the main electronics 20 is contained in the transmitter portion 3 of device 1. The handle portion 11 further includes a main control 21, battery level LEDs 12 and channel select LEDs 22, as well as the transmitter module 3 as shown in FIG. 13.

Referring now to FIGS. 4, 5, 6, and 8, the housing 2 is shown in an exploded view to illustrate the camera electronics assembly 43 separate from camera module 16. The camera electronics assembly 43 includes primary lighting elements 36 and the image sensor 34 (as shown in FIG. 5) mounted to the assembly 43 and connected by a flexible printed circuit 54 to allow for the relative movement of the image sensor frame-mounted image board 34 during focusing operations. Camera module 16 is shown electronically connected to main electronics 20, which is further connected to data link 100 and docking station 101. The focus link 31 is shown including focus adjustment slot 32 and focus control cam and track 33. Focus controls 19 are connected to focus link 31 for adjusting the focus of the camera module 16. The articulation link 25 is shown including articulation rack 24 and is connected to articulation controls 28 which change the orientation of camera module 16. Additional performance information is communicated to the operator by battery level LEDs 12 and channel select LEDs 22.

Referring specifically to FIG. 5, the imaging device 1 is shown in a side view with housing 2 removed. Camera module 16 is shown with its predetermined range of movement 102 that is up to 90 degrees relative to the horizontal plane (Y-axis) of imaging device 1. In practical terms, this predetermined range of movement 102 about the camera module pivot pin 27 enables imaging device 1 to provide the user with a field of view that ranges from 60 degrees forward (toward a patient's throat) to backward 30 degrees (toward a patient's incisors) without requiring any articulation by the user. Those having ordinary skill in the art will appreciate that the range of movement 102 as provided herein is an example and should not be construed as limiting the present invention. Rather, the predetermined range of movement 102 of the present invention may be increased based on the scale of the invention and image capture technological advances. By way of example, the predetermined range of movement 102 may be increased to 135 degrees relative to the horizontal plane of imaging device 1 where the size of the head is increased. Such increased range of movement may be found desirable in industrial applications, such as an inspection camera.

The movable image sensor frame 34 is disposed adjacent to camera module 16 and is electronically connected to main electronics 20. The image capture control 18 communicates with the main electronics 20 where it is processed and transmitted to the receiver module 4 wirelessly or via Cat5 cable and appears on imaging display device 9 as a frozen image. In operation, the device 1 provides continuous video images to the imaging display 9 through receiver module 4. When the operator has determined that the current image is one that is to be captured, the operator actuates the image capture control 18 which sends a signal to the system 200 software to capture the image or video.

As shown in FIG. 7, the imaging device 1 includes a protective sheath 50, which is illustrated as a flat configuration behind the handpiece. In use, the sheath is installed over the neck portion 13 and head portion 14 and completely conforms to the shape of the neck portion 13 and head portion 14, and is not distinguishable from the device 1 itself. Importantly, the structure of the head portion 14 and neck portion 13 are configured using the Whitcomb area rule to maintain the same circumference despite the different outer profiles. For illustrative purposes, the sheath 50 is shown over-sized relative to the device 1 but it should be understood that the sheath 50 will be form-fitting to the device 1 to provide a hygienic coverage for the device while it is being used to treat a patient. After treatment is complete, the sheath 50 is removed by the operator and discarded, to be replaced on the device 1 by a new sheath 50 for the next patient. Sheath 50 may be constructed of a plastic material suitable for medical purposes or another suitable material.

Referring now to FIGS. 10-12 the camera module 16 of the imaging device 1 is shown with the primary lighting elements 36, which include image electronics LEDs and primary lighting LEDs, connected to articulation link 25 and focus link 31. The handle portion 11 is disposed centrally in the device 1 whereas the focus controls 19 and articulation controls 28 are paired on opposite sides of the device 1 to facilitate common operation of the controls whether the device 1 is held with the camera module 16 pointing up (bottom teeth) or pointing down (top teeth) in the mouth of a patient. The focus link 31 is connected to focus controls 19 with focus link pivot pin 40 shown adjacent to camera module 16 and the imaging control 18 is shown disposed between the pair of articulation and focus controls 19 and 28, respectively. The main electronics 20 that is connected to Hall Effect sensor 41. Magnet target 42 is located within the operation range of Hall Effect sensor 41 and integrated into imaging control 18. In operation, the movement of imaging controls 18 causes magnet target 42 to move relative to Hall Effect sensor 41 resulting in a signal activating the camera module 16 to capture an image or video. The articulation control 19 actuates the articulation rack 24 and articulation pin 26 which in turn positions camera module 16 according to the user's input. In a similar manner, focus control 28 actuates focus link 31 to adjust the focus of camera module 16 according to the user's input along focus rack slot 32. Primary lighting elements 36 and optionally secondary lighting elements (not shown) are also activated by the user operating main controls 21 or the lighting elements may be controlled automatically through operation of camera module 16 or software of the imaging system 200.

As shown in FIG. 12, the main controls 21 are disposed at one end of the device 1, along with battery level LEDs 12 and channel select LEDs 22. The battery level LEDs 12 are shown connected to main electronics 20 and passing through housing via light pipes so as to be visible to an operator. Main controls 21 are also shown connected to main electronics 20 and passing through housing 2 so that an operator may actuate them as desired. Additionally, channel select LEDs 22 are shown connected to main electronics 20 and passing through housing 2 to directly display the channel selected by the user as well as any other channels being used or available. Alternatively, light pipes may be used to direct the light output from the channel select LEDs 22 to the exterior surface of the housing 2. Data link 100 is also shown connected to main electronics 20 and passing through one end of the device 1, opposite camera module 16.

FIG. 15 is another view of an embodiment of the intraoral imaging device 1, showing the device 1 connected to data link 100 and docked in docking station 101. The docking station 101 may include a number of securing features (not shown) to securely hold the device 1 in place while docked. For example, the docking station 101 may include frictional materials to grip the device securely. Alternatively, the docking station 101 may include a number of pins or other protuberances to mate with a number of opposite pins or protuberances on the imaging device 1. These devices may be mechanical and could include magnets. The docking station 101 may include indicators to provide the user with information regarding the state of the docking between the device 1 and the docking station 101. For example, an indicator light on the device 1, station 101, or both may illuminate when the docking is correctly completed. Oppositely, if docking is not correct, another indicator may illuminate providing the user with information to reset the device 1 in the docking station 101. An aural tone may also be included to indicate the docking status between the device 1 and docking station 101. Additionally or alternatively, an indicator may be provided on the imaging display device 9 or computer network to provide further information to the user regarding the docking status. The docking station 101 retains the Cat5 cable which connects to the device 1 for charging and/or data communication. The docking station 101 includes a Cat5 cable connector defeat feature that allows the device 1 to be removed from the docking station 101 without requiring the user to depress the tab on the Cat5 cable to release the device 1.

The operation of the device 1 is as follows. The system 200 includes docking station 101 which is to be securely fastened to a surface, such as a dental delivery equipment in an operatory which provides a working surface for the dentist, supplies fresh water, air, and power for numerous dental dispensers and tools. By locating the docking station 101 on dental delivery equipment, the data cable 100 connected to the docking station 101 may utilize the delivery equipment cable conduit routing to connect to the receiver module, which in turn is connected to an imaging display device 9. Alternatively, the docking station 101 may be located on another firm, stable surface that can support the weight of the device 1 and allows the device 1 to be connected electronically to an imaging device 9 or other computerized device, such as a laptop computer or mobile device. The docking station 101 includes at least one connection/data port 23 for a CAT6 cable, which provides a communication connection as well as a power connection for the device 1. Additional ports may be provided, such as USB or other such ports which may be developed for improved wired power transmission and data communications. The device 1 includes a number of battery charge level indicator lights 12, which provide the user with the battery charge level status, and also show the user that the device 1 is being charged when placed within the docking station 101, such as flashing the indicator lights.

The system 200 includes software, which may be included in a portable flash drive in the system 200 packaging, or is stored internally within the system 200 or the device 1, such that connecting a new computer to the system 200 automatically begins an installation of the software onto the new computer. Alternatively, the system 200 software may be provided on a DVD or other type of data disk, or may be downloadable from an internet website.

Additional docking stations 101 may be installed in other locations, such as other operatories in a dental office, for example. Devices 1 and docking stations 101 may be connected to a computer network through the receiver module 4 either wirelessly, via the Cat5 cable connected from receiver module 4 to the docking station 101 when charging or when connected to Cat5 cable used in hard-wired operating mode, such that images may be communicated within the network to imaging display devices 9 located in adjacent offices, waiting rooms, or conference rooms. In another example, the system 200 may provide a number of images to a large group of simultaneous viewers, such as in an educational situation, for example a dental school.

The system 200 may also use the integrated wireless communication system to transmit images from the device 1 to an imaging device 9, computer network, or a mobile device such as a laptop or mobile telephone. The system 200 includes a number of wireless channels, to allow for a number of devices 1 to be used within a local area, such as a dental office, without interference issues. For best performance, each device 1 should use a different wireless channel, selected on each device 1 using the appropriate main control 21.

The invention has been described in an illustrative manner. It is to be understood that the terminology which has been used is intended to be in the nature of words of description rather than of limitation. Many modifications and variations of the invention are possible in light of the above teachings. Therefore, within the scope of the appended claims, the invention may be practiced other than as specifically described.

What is claimed is:

1. An intraoral imaging system comprising:
   a receiver module further comprising at least one receiver for receiving image and video signals and a video processor;
   an imaging display device; and
   an intraoral imaging device, said device further comprising:
   a housing;
   a handle having a power source;
   a main electronics unit;
   a head portion having a window and a camera module that is rotatable within said head portion relative to said window, wherein said rotatable camera module further comprises a lens assembly and a movable image sensor that is movable in distal and proximal directions relative to said lens assembly;
   a neck portion depending from said head portion and conforming to the Whitcomb area rule relative to said head portion;
   a control portion operatively disposed between said neck portion and said handle, including image capture control, rotation control and focus control connected to said rotatable camera module and adapted to actuate said rotatable camera module within a predetermined range of movement and direct the distal and proximal spatial relationship between said lens assembly and said movable image sensor in response to operator input; and
   a transmission module, further comprising at least one transmitter for transmitting image and video signals.

2. The intraoral imaging system of claim 1, wherein said video processor transforms said image and video signals for output to said imaging display device.

3. The intraoral imaging system of claim 1, wherein said a window further comprises a spherical portion and curved portion in operational alignment with said rotatable camera module.

4. The intraoral imaging system of claim 1, wherein said rotatable camera module comprises a plurality of lighting elements.

5. The intraoral imaging system of claim 1, wherein said rotatable camera module comprises a plurality of lighting elements in the 400-499 nm range.

6. The intraoral imaging system of claim 1, wherein said intraoral imaging device further comprises a disposable sheath for protectively covering a portion of said imaging device.

7. The intraoral imaging system of claim 1, wherein said receiver module further comprises an antenna, at least one input and output port, and a communications link to said imaging display device.

8. The intraoral imaging system of claim 1, wherein said transmission module further comprises an antenna and at least one input and output port.

9. An intraoral imaging system comprising:
   a receiver module for receiving image and video signals; and
   an intraoral imaging device for capturing images and video and transmitting said images and video signals to said receiver module, said intraoral imaging device further comprising:
   a housing;
   a handle;
   a head portion comprising a window, a rotatable camera module disposed within said head portion and in operational alignment with said window, a pivot pin that is adapted to provide rotational movement of said rotatable camera module within said head portion, and said camera module further comprising a lens assembly and a movable image sensor that is movable in distal and proximal directions relative to said lens assembly;
   a neck portion depending from said head portion and conforming to the Whitcomb area rule relative to the head portion and having articulation and focus subassemblies disposed therein that are operatively connected to said rotatable camera module;
   a control portion operatively disposed between said neck portion and said handle comprising articulation, focus and image capture controls;
   a main electronics unit;
   a plurality of controls connected to said main electronics unit for operating said intraoral imaging device;
   a power source connected to said main electronics unit; and
   a transmitter module for communicating with said receiver module; and
   an intraoral imaging display device.

10. The intraoral imaging system of claim 9, wherein said receiver module further comprises at least one receiver for receiving image and video signals transmitted from said intraoral imaging device.

11. The intraoral imaging system of claim 9, wherein said receiver module and said intraoral imaging device communicate using audio and video signals.

12. The intraoral imaging system of claim 9, wherein said receiver module further comprises a video processor for processing images and video signals transmitted by said intraoral imaging device for output to said display device.

13. The intraoral imaging system of claim 9, wherein said intraoral imaging device further comprises a plurality of lighting elements.

14. The intraoral imaging system of claim 9, wherein said rotatable camera module comprises a plurality of lighting elements in the 400-499 nm range.

15. The intraoral imaging system of claim 9, wherein said intraoral imaging device further comprises a disposable sheath for protectively covering at least a portion of said imaging device.

16. An intraoral imaging system comprising:
an intraoral imaging device having a housing and a rotatable camera module operatively disposed within said housing and rotatable relative to said housing, an articulation assembly, a focus assembly adapted to control said camera module in response to user input, a power source, a transmitter module, a main electronics unit, and a plurality of controls connected to said power source, said transmitter module, and said main electronics unit;
an imaging display device for displaying images captured by said intraoral imaging device; and
a receiver module for receiving images from said transmitter module of said intraoral imaging device, further comprising a video processor for transforming images for output to said imaging display device,
wherein, said camera module further comprises a lens assembly and an image sensor that is movable in distal and proximal directions relative to said lens assembly to focus images within a predetermined field of view.

17. The intraoral imaging system of claim 16, wherein the rotatable camera module of said intraoral imaging device further comprises a plurality of lighting elements.

18. The intraoral imaging system of claim 16, wherein said rotatable camera module comprises a plurality of lighting elements in the 400-499 nm range.

19. The intraoral imaging system of claim 16, wherein said receiver module and said intraoral imaging device communicate using audio and video signals.

20. The intraoral imaging system of claim 16, wherein said intraoral imaging device further comprises a disposable sheath for protectively covering at least a portion of said imaging device.

* * * * *